(12) United States Patent
Jordan et al.

(10) Patent No.: US 8,030,312 B2
(45) Date of Patent: Oct. 4, 2011

(54) 5-HT1A RECEPTOR SUBTYPE AGONIST

(75) Inventors: Shaun Jordan, Germantown, MD (US);
Tetsuro Kikuchi, Tokushima (JP);
Katsura Tottori, Kamiita-cho (JP);
Tsuyoshi Hirose, Tokushima (JP);
Yasufumi Uwahodo, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 209 days.

(21) Appl. No.: 10/876,605

(22) Filed: Jun. 28, 2004

(65) Prior Publication Data
US 2004/0235860 A1 Nov. 25, 2004

Related U.S. Application Data

(62) Division of application No. 10/055,915, filed on Jan. 28, 2002, now Pat. No. 7,053,092.

(60) Provisional application No. 60/331,370, filed on Jan. 29, 2001.

(51) Int. Cl.
*A61K 31/496* (2006.01)
(52) U.S. Cl. .................................. 514/253.07
(58) Field of Classification Search .............. 514/253.07
See application file for complete search history.

(56) References Cited

U.S. PATENT DOCUMENTS

| | | | |
|---|---|---|---|
| 4,734,416 A | 3/1988 | Banno et al. | 514/253 |
| 4,764,416 A | 8/1988 | Ueyama et al. | 428/212 |
| 4,983,607 A | 1/1991 | Manoury et al. | 514/253 |
| 5,006,528 A | 4/1991 | Oshiro et al. | 514/253 |
| 5,073,377 A | 12/1991 | Alexander et al. | |
| 5,162,375 A | 11/1992 | Nicholson et al. | 514/646 |
| 5,200,410 A | 4/1993 | Traber et al. | |
| 5,385,914 A | 1/1995 | Fujioka et al. | |
| 5,504,093 A | 4/1996 | Gelfand et al. | |
| 5,652,247 A | 7/1997 | Ogawa et al. | |
| 5,691,330 A | 11/1997 | Nakao et al. | |
| 5,824,680 A | 10/1998 | Turner et al. | |
| 6,267,942 B1 | 7/2001 | Mori et al. | |
| 7,053,092 B2 | 5/2006 | Jordon et al. | |
| 2002/0076437 A1 | 6/2002 | Kothari et al. | |
| 2003/0027817 A1 | 2/2003 | Tollefson | |

FOREIGN PATENT DOCUMENTS

| | | |
|---|---|---|
| AU | 2002226752 B2 | 8/2002 |
| DE | 29 12 105 C2 | 8/1985 |
| DE | 29 12 105 C3 | 8/1985 |
| EP | 0 226 441 | 6/1987 |
| EP | 0 360 077 | 3/1990 |
| EP | 0 367 141 | 5/1990 |
| EP | 0 565 274 | 10/1993 |
| EP | 0 776 927 B1 | 6/1997 |
| JP | 54-130587 | 10/1979 |
| JP | 56-46812 | 4/1981 |
| JP | 2-191256 | 7/1990 |
| JP | A-70135 | 3/1995 |
| JP | 9-40648 | 2/1997 |
| JP | 11-508280 | 10/1997 |
| JP | 9 301 867 | 11/1997 |
| JP | 9-291034 | 11/1997 |
| JP | 09 301867 | 11/1997 |
| JP | 11-509865 | 11/1997 |
| JP | 11-335286 | 12/1999 |
| WO | WO 92/10200 | 6/1992 |
| WO | WO 92/20655 | 11/1992 |
| WO | WO 93/04681 | 3/1993 |
| WO | WO 94/09765 | 5/1994 |
| WO | WO 94/13620 | 6/1994 |
| WO | WO 98/07426 | 2/1998 |
| WO | WO 98/08817 | 3/1998 |
| WO | WO 99/38864 | 8/1999 |
| WO | WO 99/52870 | 10/1999 |
| WO | WO 02/102297 A2 | 12/2002 |
| WO | WO 03/026659 A1 | 4/2003 |
| WO | WO 03/030868 | 4/2003 |

OTHER PUBLICATIONS

Vippagunta et al. Adv. Drug Del. Rev., vol. 48, (2001), pp. 3-26.*
Sheehan et al. Acta Psychiatr. Scand., 1993, vol. 88, No. 1, pp. 1-11 (Abstract attached).*
Poltronieri et al. Behavioral Brain Research, 2003, vol. 147, pp. 185-192.*
Aouizerate et al. Neuropsychiatric Disease and Treatment, 2005, vol. 1, No. 3, pp. 231-243.*
Fujii et al. Prog. Neuropsychopharmacol. Biol. Psychiatry, Nov. 28, 2009, Issue 1878-4216 (Abstract attached).*
Garattini et al. Clin. Neuropharmacol., 1988, vol. 11, suppl. 1, pp. S8-S32 (Abstract attached).*
Gentile, Neuropsychiatric Disease and Treatment, 2009, vol. 5, pp. 117-125.*
Kohen et al. Am. J. Ther., 2009, vol. 16, No. 2, pp. 197-198 (Abstract attached).*
Manfredi et al. Am. J. Psychiatry, 1991, vol. 148, No. 9, pp. 1213-1217 (Abstract attached).*
Lykouras et al. European Neuropsychopharmacology, 2000, vol. 10, pp. 385-387.*

(Continued)

*Primary Examiner* — James Anderson
(74) *Attorney, Agent, or Firm* — Finnegan, Henderson, Farabow, Garrett & Dunner, L.L.P.

(57) ABSTRACT

The present invention relates to a method of treating a patient suffering from a disorder of the central nervous system associated with 5-$HT_{1A}$ receptor subtype, comprising as an active ingredient a carbostyril derivative or a salt thereof represented by the formula (1):

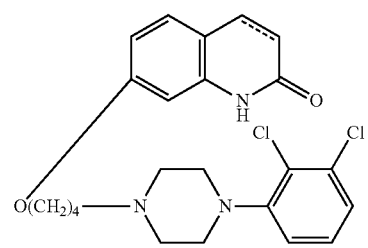

(1)

wherein the carbon-carbon bond between 3- and 4-positions in the carbostyril skeleton is a single or a double bond.

6 Claims, No Drawings

OTHER PUBLICATIONS

Lykouras et al. Progress in Neuro-Psychopharmacology & Biological Psychiatry, 2003, vol. 27, pp. 333-346.*
McDougle et al. The American Journal of Psychiatry, 1996, vol. 152, No. 12, pp. 1812-1814 (Abstract attached).*
Eric P.M. Prinssen et al., Interactions between neuroleptics and 5-HT$_{1A}$ ligands in preclinical behavioral models for antipsychotic and extrapyramidal effects, Psychopharmacology, vol. 144, No. 1, May 1999, pp. 20-29.
Uwahodo Yasufumi et al., "Pharmacological profile of OPC-14597, a novel antipsychotic drug (2); Weak extrapyramidal side effects." Japanese Journal of Pharmacology, vol. 67, No. Suppl. 1, 1995, p. 144P.
S. Jordan et al., "In Vivo Effects of Aripiprazole on Dopaminergic and Serotonergic Function in Rat Prefrontal Cortex and Striatum." Society for Neuroscience Abstracts, Society of Neurosciene, US, vol. 2., No. 27, 2001, p. 2327, AN87503.
Jeffery A. Lieberman, "Atypical Antipsychotic Drugs as a First-Line Treatment of Schizophrenia: A Rationale and Hypothesis," Journal of Clinical Psychiatry, vol. 57, No. Suppl. 11, 1996, pp. 68-71.
Paul E. Keck, Jr., et al., "Bipolar Disorder," Medical Clinics of North America, W. B. Saunders Company, Philadelphia, US., vol. 3, No. 85, May 2001, pp. 645-661.
Maria-Garcia-Anaya et al., Los antipsycoticos atipicos: Una Revisión, Salud Mental, vol. 24, No. 5, Oct. 2001, pp. 37-43.
Yamada et al., Society for Neuroscience Abstracts (2000), 26 (1-2). No.—871.7.
"Unique Pharmacological Profile of a Novel Antipyschotic Drug, Aripiprazole (OPC-14597)" M. Sasa et al., CNS Drug Reviews, 1997, vol. 3, No. 1, pp. 24-33.
"Effects of Antidepressants on 5-HT$_7$ Receptor Regulation in the Rat Hypothalamus," U. L. Mullins et al., Neuropsychopharmacology, 1999, vol. 21, No. 3, pp. 352-367.
"Alterations of Central Serotonin and Dopamine Turnover in Rats Treated with Ipsapirone and Other 5-Hydroxytryptamine$_{1A}$ Agonists with Potential Anxiolytic Properties[1]," M. Hamon et al., J. Pharmacol. Exp. Ther., 1988, vol. 246, No. 2, pp. 745-752.
"Synthesis and Structure-Activity Relationship of Substituted Tetrahydro- and Hexahydro-1,2-benzisothiasol-3-one 1,1-Dioxides and Thiadiazinones: Potential Anxiolytic Agents," M. Abou-Gharbia et al., J. Med. Chem., 1989, Vo. 32, No. 5, pp. 1024-1033.
H. Y. Meltzer et al., "Multisystems and Circuitry Pharmacotherapy—Single or Multiple Receptor Targets: Which are Best for Antipsychotic Drugs," Neuropsychopharmacology 2000, vol. 23, No. 52.
Alfieri et al., "Comparative efficacy of a single oral dose of ondansetron and of buspirone against cisplatin-induced emesis in cancer patients," British Journal of Cancel, vol. 72, 1995, pp. 1013-1015.
L.R.C. Agnew et al., "Dorland's illustrated medical dictionary, 24th Edition," 1965, W:B: Saunders Company, Philadelphia, p. 1088.
Tsutomu Inoue et al., "Effects of Novel Antipsychotic Agent 7-{4-[4-(2,3-dichlorophenyl)-1-piperazinyl]butyloxy}-3,4-dihydro-2(1H)-quinolinone (OPC-14597) on Prolactin Release from the Rat Anterior Pituitary Gland," The Journal of Pharmacology and Experimental Therapeutics, vol. 277, No. 1, Apr. 1996, pp. 137-143.
T. Sumiyoshi et al., "Tandospirone, a serotonin-1A agonist, added to neuroleptic treatment enhances cognitive performance in schizophrenia," Database accession No. PREV200200022926.
Paul J. Goodnick et al., "Aripiprazole: Profile on efficacy and safety," Expert Opinion on Pharmacotherapy, (2002) vol. 3(12) pp. 1173-1781.
Mark H. Beers, M.D. et al., "The Merck Manual of Diagnosis and therapy, Seventeenth edition", Merck Research Laboratories, Whitehouse Station, N.J., (1999) pp. 1513-1516.
Nanzando's Medical Dictionary, (1990), 17th Ed., p. 1571.
Nico J. Stam et al., "Human Serotonin 5-HT$_7$ Receptor: Cloning and Pharmacological Characterisation of Two Receptor Variants," FEBS Letters 413 (1997) 489-494.
Joyce L.W. Yau et al., "Impact of Adrenalectomy on 5- HT$_6$ and 5-HT$_7$ Receptor Gene Expression in the Rat Hippocampus," Molecular Brain Research 45 (1997) 182-186.

Murasaki, Mitsukuni, "Recent Trend of Development of Psychoactive Drugs (2)—Antipsychotic Drugs," Jpn. J. Psychopharmacol., 15(3), 191-210 (1995).
Lawler, Cindy P. et al., "Interactions of the Novel Antipsychotic Aripiprazole (OPC-14597) with Dopamine and Serotonin Receptor Subtypes," Neuropshychopharmacology, vol. 20, No. 6, p. 612-627 (1999).
Office Action in Japan Application No. 2002-560616 dated Nov. 13, 2007.
Abe, M. et al., "Effect of 5-{-[((2,S)-1,4-Benzodioxan-2-ylmethyl)amino]propoxy}-1,3-benzodioxole HCI (MKC-242), a Novel 5-HT$_{1A}$-Receptor Agonist, on Aggressive Behavior and Marble Burying Behavior in Mice," Jpn. J. Pharmacol. 76, 297-304 (1998).
Abraham, H.D. et al., "LSD-Like Panic From Risperidone in Post-LSD Visual Disorder," Journal of Clinical Psychopharmacology, vol. 16, No. 3, pp. 238-241 (1996).
Aceto, M. D. et al., Suppression of Opiate Withdrawal and Cocaine Hyperarousal Syncromes by Buspirone, Arzneim-Forsch, Drug Res., 43 (II), Nr. 9 (1993).
Affidavit of Professor Cools (2008), pp. 1-5.
Ahlenius, S. et al., "Specific Involvement of Central 5-HT$_{1A}$ Receptors in the Mediation of Male Rat Ejaculatory Behavior," Neurochemical Research, vol. 22, No. 8, pp. 1065-1070 (1997).
Aoki, S. et al., "Study on Crystal Transformation of Aripiprazol," Article presented in the 4th Japanese-Korean Symposium on Separation Technology (Oct. 6-8, 1996), pp. 937-940.
Apter, J. T. et al., << Buspirone : Future Directions, >> Journal of Clinical Psychopharmacology, vol. 19, No. 1, pp. 86-93 (1999).
Arkle, Marion et al.,"Ipsapirone Suppresses Food Intake in Food-Deprived Rats by an Action at 5-HT$_{1A}$ Rceptors," European Journal of Pharmacology, vol. 408, pp. 273-276 (2000).
Bjorvatn B. et al., "Sleep/waking effects of a selective 5-HT$_{1A}$ receptor agonist given systemically as well as perfused in the dorsal raphe nucleus in rats," Brain Research, 770, 81-88 (1997).
Brittain, H.G., "Polymorphism in Pharmaceutical Solids," New York (1999), pp. 334-335.
Brittain, H.G., "Spectral Methods for the Characterization of Polymorphs and Solvates," Journal of Pharmaceutical Sciences, Apr. 1997, vol. 86, No. 4, pp. 405-412.
Caira, M.R., "Crystalline Polymorphism of Organic Compounds," (1998), pp. 165-166.
Canive, J.M. et al., "Spontaneous Brain Magnetic Activity in Schizophrenia Patients Treated With Aripiprazole," Psychopharmacol Bull. 1998;34(1):101-5.
Cervo L. et al., "Effects of dopaminergic and glutamatergic receptor antagonists on the establishment and expression of conditioned locomotion to cocaine in rats," Brain Research, 739, 31-38 (1996).
Ebenezer, Ivor et al., "Effects of the 5-HT$_{1A}$ Receptor Agonist 8-OH-DPAT on Operant Food Intake in Food-Deprived Pigs," Physiology & Behavior, vol. 67, No. 2, pp. 213-217 (1999).
Ecuadorian Institute of Intellectual Property Patentability Examination Report for Application No. SP 06 6521, dated Sep. 5, 2008.
Ecuadorian Institute of Intellectual Property Patentability Examination Report for Application No. SP 06 6522, dated Sep. 19, 2008.
Elvevag, B. et al., "Cognitive Impairment in Schizophrenia Is the Core of the Disorder," Critical Reviews in Neurobiology 2000, 14(1), 1 to 21.
Fedoroff, J. Paul et al., "Buspirone Hydrochloride in the Treatment of an Atypical Paraphilia,"Archives of Sexual Behavior, vol. 21, No. 4, pp. 401-406 (1992).
Ferrari, F. et al., "The Selective D$_2$ Dopamine Receptor Antagonist Eticlopride Counteracts the Ejaculatio Praecox Induced by the Selective D$_2$ Dopamine Agonist SND 919 in the Rat," Life Sciences, vol. 55, No. 14, pp. 1155-1162 (1994).
Foreman, Mark et al., "Preclinical Studies on LY228729: A Potent and Selective Serotonin$_{1A}$ Agonist," Journal of Pharmacology and Experimental Therapeutics, vol. 267, No. 1, pp. 58-71 (1992).
Fratta, W. et al., "Stress-induced insomnia: opioid-dopamine interactions," European Journal of Pharmacology, 142, 437-440 (1987).

Forbes et al.; "(R)-3, N-Dimethyl-N-[1-Methyl-3-(4-Methyl-Piperidin-1-YL)Propyl]Benzenesulfonamide: The First Selective 5-HT$_7$ Receptor Antagonist"; Journal of Medical Chemistry, vol. 41, No. 5, pp. 655-657, (1998).

Geretsegger, Christian, "Ipsapirone in the Treatment of Bulimia Nervosa: An Open Pilot Study," International Journal of Eating Disorders, vol. 17, No. 4, pp. 359-363 (1995).

Giannini, J. A. et al., << Behavioral Response to Buspirone in Cocaine and Phencyclidine Withdrawal, Journal of Substance Abuse Treatment, vol. 10, pp. 523-527 (1993).

Haensel, Stefan et al., "Flesinoxan: a Prosexual Drug for Male Rats," European Journal of Pharmacology, vol. 330, pp. 1-9 (1997).

Harwood, L. et al., "Experimental Organic Chemistry Principles and Practice," Blackwell Scientific Publications (1989), pp. 136-137.

Inoue, A. et al., "Differential Effects on $D_2$ Dopamine Receptor and Prolactin Gene Expression by Haloperidol and Aripiprazole in the Rat Pituitary," Molecular Brain Research 1998, 55, 285-292.

Kane, J.M. et al., "Efficacy of Aripiprazole in Psychotic Disorders: Comparison With Haloperidol and Placebo," Int J Neuropsychopharmacol 2000 3; Suppl 1:Abst P01.124.

Kay, Stanley et al., "The Positive and Negative Syndrome Scale (PANSS) for Schizophrenia," Schizophrenia Bulletin 13: 261-276 (1987).

Keck, P.E., Jr., "Treatment Advances in Bipolar Disorder—Making Up for Lost Time," Biological Psychiatry 48(b) 430-432 (2000).

Keefe, R.S. et al., "The Effects of Atypical Antipsychotic Drugs on Neurocognitive Impairment in Schizophrenia: A Review and Metanalysis," Schizophr Bull 1999:25:201-222.

Kern, R.S. et al., "An Open-label Comparison of the Neurocognitive Effects of Aripiprazole Versus Olanzapine in Patients With Stable Psychosis," Schizophr Res 2001 49(1-2); Suppl S:234.

Mallikaarjun S et al., "The Pharmacokinetics, Tolerability, and Safety of Aripiprazole Following Single and Multiple Oral Dose Administration," Int J. Neuropsychopharmacol 2000 3; Suppl 1:Abst P01.123.

Matuszewich, L. et al., "Partial antagonism of 8-OH-DPAT'S effects on male rat sexual behavior with a $D_2$, but not a 5-HT$_{1A}$, antagonist," Brain Research, 820, 55-62 (1999).

Mendelson, W., "Effects of Buspirone on Sleep and Respiration[1,2]," Am. Rev. Respir. Dis. 141:1527-1530 (1990).

The Merck Index—Aripiprazole (2001).

Millan, M.J. et al., "Improving the Treatment of Schizophrenia: Focus on Serotonin (5-HT)(1A) Receptors," J. Pharmacol. Exp. Ther. Dec. 2000; 295(3):853-61.

Mohs, R.C., "Cognition in Schizophrenia: Natural History, Assessment, and Clinical Importance," Neuropsychopharmacology 1999, 21(6), pp. 203-210.

Molewijk. H. E. et al., "Conditioned ultrasonic distress vocalizations in adult male rats as a behavioural paradigm for screening anti-panic drugs," Psychopharmacology, 117: 32-40 (1995).

Monti, J.M. et al., "Role of Dorsal Raphe Nucleus Serotonin 5-HT$_{1A}$ Receptor in the Regulation of Rem Sleep," Life Sciences, vol. 66, No. 21, pp. 1999-2012 (2000).

Monti J. M. et al, "Sleep and Waking in 5,7-DHT-Lesioned or (−)-Pindolol-Pretreated Rats After Administration of Buspirone, Ipsapirone, or Gepirone," Pharmacology Biochemistry and Behavior, vol. 52, No. 2, pp. 305-312 (1995).

Novelli, Emanuela et al., "A Molecular Investigation Suggests No Relationship Between Obsessive-Compulsive Disorder and the Dopamine $D_2$ Receptor," Neuropsychobiology, vol. 29, pp. 61-63 (1994).

Odagaki, Yuki et al., "5-H$_{1A}$ Receptor Agonist Properties of Antipsychotics Determined by [$^{35}$S] GTPγs Binding in Rat Hippocampal Membranes," Clinical and Experimental Pharmacology and Physiology, vol. 34, p. 462-466 (2007).

Oshiro, Y. et al., "Novel Antipsychotic Agents With Dopamine Autoreceptor Agonist Properties: Synthesis and Pharmacology of 7-[4-(4-Phenyl-1-piperazinyl)butoxyl]-3,4-dihydro-2(1H)-Quinolinone Derivatives," Journal of Medicinal Chemistry, American Chemical Society, Washington, US, vol. 41, No. 5, Feb. 26, 1998, pp. 658-667.

Parada, Marco et al., "Rats Self-Inject a Dopamine Antagonist in the Lateral Hypothalamus Where It Acts to Increase Extracellular Dopamine in the Nucleus Accumbens," Pharmacology Biochemistry and Behavior, vol. 52, No. 1, pp. 179-187 (1995).

Petrie, J.L., "Acute and Long-Term Efficacy and Safety of Aripiprazole: A New Atypical Antipsychotic," Schizophrenia Research 1998, 29 (1-2), 155.

F. Puel et al., Polymorphism in Fine Organic Processes, LAGEP UMR CNRS 5007, Université Lyon 1, SCPE. Bât. 308G, 43 Bd. du Nov. 11, 1918. F-69622 Villeurbanne, France.

Purdon, S.E., "Long-Term Treatment With Quetiapine Improves Cognitive Function in Schizophrenia," Biol. Psychiatry 2000, 47, p. 42.

Rawla, A., "Basic Principles of Particle Size Analysis," published by Malvern Instruments, pp. 1-8 (2007).

Rivas-Vazquez, R.A. et al., "Atypical Antipsychotic Medications: Pharmacological Profiles and Psychological Implications," Professional Psychology: Research and Practice 2000, 31(6), 628-640.

Rund, B.R. et al., "How Do Neuroleptics Affect Cognitive Dysfunctions in Schizophrenia?," Nord. J. Psychiatry 1999, 53(2), 121 to 125.

Saha A.R., et al., "Safety and Efficacy Profile of Aripiprazole, a Novel Antipsychotic," Schizophr Res 1999 36:1-3:295.

Schafer, D. et al., "Effects of parkinsonian medication on sleep," J Neurol, 247 [Suppl 4]:IV/24-IV/27 (2000).

SCRIP News Letter 2000 No. 2580, p. 11 (Oct. 4, 2000).

Seifritz E. et al., "The 5-HT$_{1A}$ agonist ipsapirone enhances EEG slow wave activity in human sleep and produces a power spectrum similar to 5-HT, blockade," Neuroscience Letters 209, 41-44 (1996).

Serper, M.R. et al., Novel Neuroleptics Improve Attentional Functioning in Schizophrenic Patients : Ziprasidone and Aripiprazole, CNS Spectrums 2(8): 56-59 (1997).

Sumiyoshi T. et al., "Tandospirone, a Serotonin-1A Agonist, Added to Neuroleptic Treatment Enhances Cognitive Performance in Schizophrenia," Biosciences Information Service, Philadelphia, PA, US (2001).

Tamai, Hajime et al., "The Clinical Efficacy of a 5-HT$_{1A}$ Agonist, SM-3997, In the Treatment of Bulmina," International Journal ob Obesity, vol. 14, pp. 289-292 (1990).

The United States Pharmacopeia (USP) 29, (2006), pp. 2788-2789.

Tunnicliff, G., "Molecular Basis of Buspirone's Anxiolytic Action," Pharmacology & Toxicology, 69, 149-156 (1991).

Wolfgang Beckmann, "Seeding the Desired Polymorph: Background, Possibilities, Limitations, and Case Studies," Chemical Engineering Department, Chemical Development, Schering AG, 13342 Berlin, Jul. 6, 2000.

Zhang, Han-Ting, "Regulation of the Central Opioidergic Nervous System on the Emotional State of Anxiety and its Possible Mechanisms," Institute of Pharmacology and Toxicology, Academy of Military Medical Sciences (1997).

Communication of a Notice of Opposition (Apr. 10, 2008).

Novelty Search Report from Hungarian Application No. P0600141 dated Feb. 19, 2008.

Translation of Opposition Brief dated Feb. 25, 2008.

Aguirre, E.M., "Introduction a la Tecnologia Farmaceutica," vol. 1, pp. 92, 96, and 117 (1989) (translation).

Aulton, M.E., "Pharmaceuticals: The Science of Dosage Form Design," Churchill Livingstone, Inc.: New York, 1988, pp. 8-9 and 223-226.

Brittain, H.G., "Polymorphism in Pharmaceutical Solids," Marcel Dekker, Inc.: New York, 1999, pp. 235-237 and 270-271.

Columbian Office Action of Dec. 28, 2007, (translation).

Columbian Office Action of Jul. 3, 2009, (translation).

Comparison of PXRD spectra—Hydrate A and MAB-1541 with matching scales.

Comparison of PXRD spectra—Hydrate A and MAB-1541 with spectra aligned to take account of systematic error.

European Medicine Agency (EMEA) Report on Aripiprazole, 2005, pp. 1-29.

Helman, J., "Farmacotecnia Teórica y Práctica. Tomo IV," CIA. Editorial Continental, S.A., de C.V., pp. 1142 and 1165 (1982).

Hosino, Y. et al., "Blood Serotonin and Free Tryptophan Concentration in Autistic Children," Neuropsychobiology, vol. 11, pp. 22-27 (1984).

Jing Kang Wang et al., "The Effect of Physical Environment of Crystallization Process on the Polymorph of Ciprofloxaun Hydrochloride," School of Chemical Engineering and Technology, Tianjin University, Tianjin, 300072, P.R. China (2002).
King, R., "Preparados farmacéuticos y su elaboración," Remington 2: Farmacia, Editorial Medica Panamericana S.A., pp. 1910-1920 (1987).
Notice of Opposition by Fermion Oy, date Jan. 4, 2007 (28 pages).
Opposition Proceedings in EP 1 330 249: Letter from Opponent dated Apr. 17, 2009, by Opponent I Teva Pharmaceuticals (12 pages).
Opposition Proceedings in EP 1 330 249: Letter from Opponent dated Apr. 17, 2009, by Opponent IV Egis Gyógyszergyar Nyrt (18 pages).
Perry, J.H., "Manual de Ingeniero Quimico," vol. 1, 3$^{rd}$ Edition, pp. 1239 (1981) (translation).
Rhodes, M., "Introduction to Particle Technology," John Wiley & Sons: England, 1998, pp. 69-70.
Wade, A. et al., "Handbook of Pharmaceutical Excipients," Second Ed., The Pharmaceutical Press: England, 1994, pp. 1-2.
Zakrzewski, A. et al., "Solid State Characterization of Pharmaceuticals," Assa International Inc.: Connecticut, 2006, pp. 134-135 and 152.
Abstract of Hoshino et al., "Blood serotonin and free tryptophan concentration in autistic children," Neuropsychobiology, 11(1):22-27 (1984).
Boast et al., "5HT Antagonists Attenuate MK801-Impaired Radial Arm Maze Performance in Rats," Neurobiology of Learning and Memory, 1999, vol. 71, pp. 259-271.
Friedman et al., Open-label Flexible-Dose Pilot Study to Evaluate the Safety and Tolerability of Aripiprazole in Patients With Psychosis Associated With Parkinson's Disease, Movement Disorders, 2006, vol. 21, No. 12, pp. 2078-2081.
Hammerstad et al., "Buspirone in Parkinson's Disease," Clin. Neuropharmacol., 1986, vol. 9, No. 6, pp. 556-560. (Abstract).
Wickremaratchi et al., "Aripiprazole Associated with Severe Exacerbation of Parkinson's Disease," Movement Disorders, 2006, vol. 21, No. 9, pp. 1538-1539.
Bauer, K.H. et al, "Pharmazeutische Technologie," Georg Thieme Verlag, Stuttgart, 1986, pp. 75-81.
Beers, M.H. et al., "Ther Merck Manualof Diagnosis and Therapy," 17$^{th}$ Ed., 1999, pp. 2233-2236.
Connor, K.M. et al., "The Use of Aripiprazole in Obsessive-Compulsive Disorder: Preliminary Observations in 8 Patients," J. Clin. Psychiatry, 2005, 66(1): 49-51.
Decision Revoking European Patent, European Patent Office, regarding European Patent No. 1 330 249, dated Jul. 7, 2009.
Fujii, A. et al., "Sexual dysfunction in Japanese patients with schizophrenia treated with antipsychotics," Prog. Neuro-Pyschopharmacol. Biol. Pyschiatry., 2009, Article in Press (Full Article).
Garattini, S. et al., "Progress in assessing the role of serotonin in the control of food intake," Clin. Neuropharmacol., 1988, 11(Supp 1): S8-32 (Full Article).
Harata, T. et al., "Aripiprazole Augmentation for a Patient With Partial Remission of Panic Disorder," J. Clin. Psychopharmacology, Letters to the Editor, 2009, 29(3): 301-302.
Hoge, E. A. et al., "Aripiprazole as Augmentation Treatment of Refractory Generalized Anxiety Disorder and Panic Disorder," CNS Spectr. 2008, 13(6): 522-527.
Kohen, T. et al., "Central sleep apnea in a geriatric patient treated with aripiprazole," Am. J. Ther., 2009, 16(2): 197-198 (Full Article).
Manfredi, R.L. et al., "Dr. Manfredi and Associates Reply," Am. J. Psychiatry, Letters to Editor, 1993, 150(5): 845-846.
Office Action in U.S. Appl. No. 11/932,795 dated Apr. 15, 2009.
Office Action in U.S. Appl. No. 11/932,795 dated Dec. 17, 2009.
Office Action in U.S. Appl. No. 12/202,192 dated Jan. 7, 2010.
Office Action in U.S. Appl. No. 12/202,201 dated Oct. 20, 2009.
Office Action in U.S. Appl. No. 12/202,208 dated Feb. 18, 2010.
Opposition in EP 1 330 249 by Opponent IV Egis Gyógyszergyár Nyrt. dated Mar. 13, 2010 (17 pages) including Supplemented List of Cited Documents (2 pages) and Attachment D33c (1 page).
Opposition in Indian Patent Application No. IN/PCT/2002/1536 dated Jan. 8, 2010, by Torrent Pharmaceuticals Ltd., including Exhibits 1A, 3A-3C, and 5 (67 pages).
Pessina, E. et al., "Aripiprazole augmentation of serotonin reuptake inhibitors in treatment-resistant obsessive-compulsive disorder: a 12-week open-label preliminary study," Int. Clin. Psychopharmacol., 2009, 24: 265-269.
Revised Opposition Data from Teva Pharmaceuticals Industries Limited, regarding European Patent No. 1 330 249, dated Apr. 18, 2008.
Summons to Attend Oral Proceedings from European Patent Office, regarding European Patent No. 1 330 249, dated Jan. 27, 2009.
Summons to Attend Oral Proceedings from European Patent Office, regarding European Patent No. 1 621 198, dated Oct. 13, 2009.
Test Reports from National Commission of Atomic Energy, including Test Report No. 33 of the X-Ray Diffraction Laboratory of the National Commission of Atomic Energy, dated Aug. 25, 2003, Argentina; Experimental Report on Aripiprazole, Nov. 17, 2003, Buenos Aires; and Test Report No. 32 of the X-Ray Diffraction Laboratory of the National Commission of Atomic Energy, dated Aug. 20, 2003, Argentina.
Ajit, "Does Aripiprazole Have a Role in Treating Cognitive Impairment in Parkinson's Disease," J. Neuropsychiatry Clin. Neurosci., 2007, 19(2): 205-206.
Carli et al., "S 15535, a benzodioxopiperazine acting as presynaptic agonist and postsynaptic 5-HT1A receptor antagonist, prevents the impairment of spatial learning caused by intrahippocampal scopolamine," British J. Pharmacology, 1999, 128: 1207-1214.
Carli et al., "Stimulation of 5-HT1A receptors in the dorsal raphe reverses the impairment of spatial learning caused by intrahippocampal scopolamine in rats," European J. Neuroscience, 1998, 10: 221-230.
Cole et al., "5-HT1A receptor agonists improve the performance of normal and scopolamine-impaired rats in an operant delayed matching to position task," Pyschopharmacology, 1994, 116: 135-142.
Communication from European Patent Office dated Apr. 12, 2010, forwarding a letter from Opponent 03, Pharmaceutical Works POLPHARMA, dated Mar. 22, 2010, regarding the Appeal of EP Patent No. 1 330 249, including • Document D15a—Handwritten amended reference numbers on experimental results obtained in 2006 provided by Opponent 03 and enclosed to his Notice of Opposition of Jan. 5, 2007; • Document D15b—IR absorption spectrum (KBr) of sample A1 and TGA of sample A2, 2006; • Document D15c—Comparison of experimental results obtained in 2006 by Opponent 03 with results of 2010 for the samples prepared in 2006 according to the Opposed Patent; • Documents D34—Brittian, "Polymorphism in Pharmaceutical Solids," Drugs and the Pharmaceutical Science, vol. 95, Chapter entitled: "Methods for the Characterization of Polymorphs—X-ray Powder Diffraction," p. 235-238; and • Document D35—A.N. Planowski et al. "Procesy i paraty w technologii chemiczej," WNT, Warswa (1974) p. 765-771 (with translation).
Communication from European Patent Office dated Apr. 12, 2010, forwarding a letter from Opponent 01, Teva Pharmaceutical Industries Limited, dated Mar. 29, 2010, regarding the Appeal of EP Patent No. 1 330 249.
Findling et al. "Aripiprazole in Children with Attention-Deficit/Hyperactivity Disorder," J. Child and Adolescent Psychopharma., 2008, 18(4): 347-354.
Galeotti et al., "Role of 5-HT1A Receptors in Mouse Passive Avoidance Paradigm," Jpn. J. Pharmacol., 2000, 84: 418-424.
Hammerstad et al., "Buspirone in Parkinson's Disease," Clin. Neuropharmacol., 1986, 9(6): 556-60 (Full Article).
Malhotra et al., "An Open Clinical Trial of Buspirone in Children with Attention-Deficit/Hyperactivity Disorder," J. Am. Acad. Child Adolesc. Psychiatry, 1998, 37(4): 364-371.
McCormick, "Treatment with Buspirone in a Patient with Austism," Arch. Fam. Med., 1997, 6: 366-370.
McDougle et al., "Atypical Antipsychotics in Children and Adolescents with Autistic and Other Pervasive Developmental Disorders," J. Clin. Psychiatry, 2008, 69(Supp 4): 15-20.
McElroy et al., "Pharmacological Agents for the Treatment of Acute Bipolar Mania," Biol. Psychiatry, 2000, 48: 539-557.
Micheau et al., "Stimulation of 5-HT1A Receptors by Systemic or Medial Septum Injection Induces Anxiogenic-like Effects and Facilitates Acquisition of a Spatial Discrimination Task in Mice," Prog. Neuro-pyschopharmacol & Biol. Psychiat., 1999, 23: 1113-1133.

Office Action (Ex Parte Quayle Action) in U.S. Appl. No. 12/202,201 dated Jun. 1, 2010.
Realmuto et al. "Clinical Effect of Buspirone in Autistic Children," J. Clin. Pyschopharmacol., 1989, 9(2): 122-125.
Remington Farmacia, 2000, 20th Edition, pp. 824 and 828.
Seidl et al., "Serotonin (5-HT) in brains of adult patients with Down Syndrome," J. Neural. Transm., 1999, 57(supp): 221-232.
Sheehan et al., "The relative efficacy of high-dose buspirone and alprazolam in the treatment of panic disorder: a double-blind placebo-controlled study," Acta Psychiatr. Scand. 1993, 88: 1-11 (full article).
Stigler et al., "Case Report: Aripiprazole for Maladaptive Behavior in Pervasive Development Disorders," J. Child and Adolescent Pyschopharmacology, 2004, 14(3): 455-463.
Summons to Attend Oral Proceedings from European Patent Office, regarding European Patent Application No. 06015782.3, dated Apr. 12, 2010.
Translation of A.N. Planowski et al. "Procesy i paraty w technologii chemiczej," WNT, Warswa (1974) p. 765-771.
Ward et al., "Forebrain serotonin depletion facilitates the acquisition and performance of a conditional visual discrimination task in rats," Behavioral Brain Research, 1999, 100: 51-65.
Excerpt from Examination Guidelines for Patent and Utility Model in Japan, Part VII: Examination Guidelines for Inventions in Specific Fields, Ch. 3 Medicinal Inventions, p. 5.
English translation of excerpt from Examination Guidelines for Patent and Utility Model in Japan, Part VII: Examination Guidelines for Inventions in Specific Fields, Ch. 3 Medicinal Inventions, p. 5 (page 7 of translation).
"Aripiprazole OPC 14597," Drugs R & D, 1999, vol. 2, No. 1, pp. 47-48.
Bristol-Myers Squibb Press Release, "New Data Presented Today at American Psychiatric Association Annual Meeting," May 22, 2002.
Findling et al., "An open clinical trial of risperidone monotherapy in young children with autistic disorder," Psychopharmacol. Bull., 1997, 33(1):155-159 (Abstract).
Frye et al., "Clozapine in bipolar disorder: treatment implications for other atypical antipsychotics," Journal of Affective Disorders, 1998, 48:91-104.
McDougle et al., A Double-blind, Placebo-controlled Study of Risperidone in Adults with Autistic Disorder and Other Pervasive Development Disorders, Arch. Gen. Psychiatry, 1998, 55:633-641.
Notice of Information Disclosure by Third Party issued by the Japanese Patent Office in Japanese Patent Application No. 2007-179275 on May 31, 2010.
English translation of Notice of Information Disclosure by Third Party issued by the Japanese Patent Office in Japanese Patent Application No. 2007-179275 on May 31, 2010.
Office Action in Taiwanese Patent Application No. 098116881 dated May 17, 2010.
English translation of an Office Action issued in Taiwanese Patent Application No. 098116881 dated May 17, 2010.
Office Action in U.S. Appl. No. 11/932,795 dated Jun. 14, 2010.
Office Action in U.S. Appl. No. 12/202,208 dated Jun. 14, 2010.
Potenza et al., "Olanzapine treatment of children, adolescents, and adults with pervasive developmental disorders: an open-label pilot study," J. Clin. Psychopharmacol., 1999, 19(1):37-44 (Abstract).
Tramontina et al., "Aripiprazole in Juvenile Bipolar Disorder Comorbid with Attention-Deficit/Hyperactivity Disorder: An Open Clinical Trial," CNS Spectr., 2007, 12(10):758-762.
Communication from European Patent Office dated Jul. 8, 2010, forwarding Maiwald's statement setting forth grounds of appeal for European Application Patent No. 05023971.4 (EP 1 621 198) dated Jun. 29, 2010.
English translation of communication from European Patent Office dated Jul. 8, 2010, forwarding Maiwald's statement setting forth grounds of appeal for European Application Patent No. 05023971.4 (EP 1 621 198) dated Jun. 29, 2010.
European Patent Office Submission of TEVA Pharmaceutical Ind., Ltd., submitting facts and arguments in the appeal of European Patent Application No. 05023971.4 (EP 1 621 198), dated Jun. 29, 2010.
European Patent Office Communication of a notice of opposition for EP Application No. 04002427.5-2101/ EP Patent No. 1419776, dated Jan. 19, 2011, forwarding TEVA Pharmaceutical Industries Ltd.'s Jan. 13, 2011, submission including Experimental Report 1 and Annexes 1-3.
Brittain, H.G., "Polymorphism in Pharmaceutical Solids," Drugs and the Pharmaceutical Science, vol. 95, Chapter entitled: "Methods for the Characterization of Polymorphs—X-Ray Powder Diffraction," pp. 235-238 (D34), 1999.
English Abstract of JP 56-46812 published Apr. 28, 1981.
English Translation of Schmidt, Martin U., "Aripiprazol Experimental Report" and Attachments I and II, Dec. 23, 2006.
English Translation of Striegel, Hans-Gunter, "Aripiprazol Experimental Report," Dec. 21, 2006.
European Patent Office Submission of RATIOPHARM GMBH in Opposition to European Patent No. 1330249, transmitted Jul. 2, 2010.
English translation of European Patent Office Submission of RATIOPHARM GMBH in Opposition to European Patent No. 1330249, transmitted Jul. 2, 2010.
Examination Report Aripiprazole by Roland Boese, dated May 31, 2010 (Document D36 referenced in the European Patent Office Submission of RATIOPHARM GMBH in Opposition to European Patent No. 1330249, transmitted Jul. 2, 2010).
English translation of Examination Report Aripiprazole by Roland Boese, dated May 31, 2010, (Document D36 referenced in the European Patent Office Submission of RATIOPHARM GMBH in Opposition to European Patent No. 1330249, transmitted Jul. 2, 2010).
European Patent Office Submission of RATIOPHARM GMBH in Opposition to European Patent No. 1330249, dated Jul. 21, 2010, submitting Projektbericht Aripiprazol by Roland Boese and Carsten Schauerte (Document D37 referenced in the European Patent Office Submission of RATIOPHARM GMBH in Opposition to European Patent No. 1330249, transmitted Jul. 2, 2010).
English translation of European Patent Office Submission of RATIOPHARM GMBH in Opposition to European Patent No. 1330249, transmitted Jul. 21, 2010, submitting Projektbericht Aripiprazol by Roland Boese and Carsten Schauerte (Document D37 referenced in the European Patent Office Submission of RATIOPHARM GMBH in Opposition to European Patent No. 1330249, transmitted Jul. 2, 2010).
Laboratory Report by Ratiopharm, dated Sep. 22, 2008 (Document D38 referenced in the European Patent Office Submission of RATIOPHARM GMBH in Opposition to European Patent No. 1330249, transmitted Jul. 2, 2010).
English translation of Laboratory Report by Ratiopharm, dated Sep. 22, 2008 (Document D38 referenced in the European Patent Office Submission of RATIOPHARM GMBH in Opposition to European Patent No. 1330249, transmitted Jul. 2, 2010).
Examiner's Re-examination Report dated Jan. 28, 2009, for Australian Patent No. 2002226752.
Examiner's Re-examination Report dated Oct. 10, 2006, for Australian Patent No. 2002334413.
Examiner's Re-examination Report dated Jan. 28, 2009, for Australian Patent No. 2002334413.
Examiner's Re-examination Report dated Jan. 28, 2009, for Australian Patent No. 2005201772.
Experimental Report (Aripiprazole Hydrate A), from EPO Decision of Jul. 7, 2009, regarding Application No. 02782507.4-2101/1330249.
Experimental Results (D3), from Notice of Opposition—Pharmaceutical Works POLPHARMA , Jan. 16, 2007, European Patent Office, Application No. 02782507.4-2101/1330249.
Jordan, S. et al., "In Vivo Effects of Aripiprazole on Cortical and Striatal Dopaminergic and Serotonergic Function," European Journal of Pharmacology, 2004, 483: 45-53.
Laitinen, Ilpo, "Experimental Report on Aripiprazole Batches," Dec. 18, 2006, Espoo, Finland.
Notice of Opposition—EGIS Gyógyszergyár Nyrt, transmitted Jan. 15, 2007, by European Patent Office in Application No. 02782507.4-2101/1330249.
English Translation of Notice of Opposition—EGIS Gyógyszergyár Nyrt, transmitted Jan. 15, 2007, by European Patent Office in Application No. 02782507.4-2101/1330249.

Notice of Opposition—Pharmaceutical Works POLPHARMA, transmitted Jan. 16, 2007, by European Patent Office in Application No. 02782507.4-2101/1330249.

Notice of Opposition—OV ratiopharm GmbH, transmitted Jan. 15, 2007, by European Patent Office in Application No. 02782507.4-2101/1330249.

English Translation of Notice of Opposition—OV ratiopharm GmbH, transmitted Jan. 15, 2007, by European Patent Office in Application No. 02782507.4-2101/1330249.

Notice of Opposition—Teva Pharmaceutical Industries Limited, transmitted Jan. 10, 2007, by European Patent Office in Application No. 02782507.4-2101/1330249.

Nousiainen, Jaako, "Aripiprazole—Analytical Investigation," Dec. 19, 2006, Fermion Oy.

Office Action in U.S. Appl. No. 10/333,244 dated Feb. 26, 2007.
Office Action in U.S. Appl. No. 10/333,244 dated Jun. 11, 2008.
Office Action in U.S. Appl. No. 10/333,244 dated Apr. 29, 2009.
Office Action in U.S. Appl. No. 11/790,604 dated Sep. 29, 2009.
Office Action in U.S. Appl. No. 11/790,604 dated May 24, 2010.
Office Action in U.S. Appl. No. 11/790,605 dated Apr. 26, 2010.
Office Action in U.S. Appl. No. 11/790,606 dated Dec. 11, 2009.
Office Action in U.S. Appl. No. 11/790,603 dated Dec. 28, 2009.
Office Action in U.S. Appl. No. 11/797,019 dated Jan. 7, 2010.
Office Action in U.S. Appl. No. 11/797,024 dated Jan. 25, 2010.
Office Action in U.S. Appl. No. 11/797,030 dated Mar. 10, 2010.
Office Action from Japanese Patent Office issued in Japanese Patent Application No. 2007-179275 on Oct. 22, 2010.
English translation of the Office Action from Japanese Patent Office issued in Japanese Patent Application No. 2007-179275 on Oct. 22, 2010.

Perez, Marina G., "Experimental Report on Aripiprazole," Nov. 17, 2003.

Request for Re-examination by Paul Jones of Australian Patent No. 2002226752 (Sep. 19, 2008).

Request for Re-examination by Paul Jones of Australian Patent No. 2002334413 (Sep. 19, 2008).

Request for Re-examination by Paul Jones of Australian Patent No. 2005201772 (Sep. 19, 2008).

Schmidt, Martin U., "Aripiprazol Experimental Report" and Attachments I and II, Dec. 23, 2006.

Statement of Grounds of Opposition filed on Dec. 17, 2010, for Australian Patent No. 2007201701 by Alphapharm Pty. Ltd.

Striegel, Hans-Gunter, "Aripiprazole Experimental Report," Dec. 21, 2006.

Tanninen, Veli Pekka, "Test Report on Aripiprazole," Orion Corporation, Orion Pharma, Dec. 19, 2006.

Tetsuro Kikuchi et al., "Pharmacological profile of OPC-14597, a novel antipsychotic drug (1): Presynaptic dopamine autoreceptor agonistic activity and postsynaptic dopamine D2 receptor antagonistic activity," Japanese Journal of Pharmacology, vol. 67, No. Suppl. 1, 1995, p. 144P.

Translation of JP 2001-290645 filed Sep. 25, 2001 (D16 from EPO Decision of Jul. 7, 2009, regarding Application No. 02782507.4-2101/1330249).

Office Action in U.S. Appl. No. 11/932,795 dated Feb. 18, 2011.
Office Action in U.S. Appl. No. 12/202,208 dated Feb. 24, 2011.
Amended Statement of Grounds of Opposition filed Mar. 17, 2011, for Australian Patent No. 2007201701 by Alphapharm Pty. Ltd.

Statutory Declaration by James Ellsmore filed in support of the Amended Statement of Grounds of Opposition filed Mar. 17, 2011, for Australian Patent No. 2007201701 by Alphapharm Pty. Ltd (including exhibits JE1-JE8).

Statutory Declaration by Julian Parmegiani filed in support of the Amended Statement of Grounds of Opposition filed Mar. 17, 2011, for Australian Patent No. 2007201701 by Alphapharm Pty. Ltd (including exhibits JE1-JE17).

Office Action from Japanese Patent Office issued in Japanese Patent Application No. 2007-179275 on Apr. 13, 2011.

English translation of the Office Action from Japanese Patent Office issued in Japanese Patent Application No. 2007-179275 on Apr. 13, 2011.

Office Action in U.S. Appl. No. 12/830,740 dated May 27, 2011.

* cited by examiner

5-HT1A RECEPTOR SUBTYPE AGONIST

CROSS REFERENCE TO RELATED APPLICATION

This application is a division of U.S. application Ser. No. 10/055,915 filed Jan. 28, 2002 now U.S. Pat. No. 7,053,092 which claims the benefit of U.S. Provisional Application Ser. No. 60/331,370 filed Jan. 29, 2001, the contents of both of which are incorporated herein by reference.

BACKGROUND OF THE INVENTION

1. Field of the Invention

The present invention relates to a method of treating a patient suffering from a disorder of the central nervous system associated with the 5-$HT_{1A}$ receptor subtype. The active ingredient comprise a carbostyril derivative or a salt thereof.

2. Related Art

U.S. Pat. No. 5,006,528; European Patent No. 367,141 and Japanese Patent Kokai (Laid-open) 7-304,740 (1995) contain the same chemical structural formula as the carbostyril derivatives in the present invention, and their pharmacological properties are beneficial drug treatments for schizophrenia.

Carbostyril compounds, as well as those disclosed in Japanese Patent Kokai (Laid-open) 9-301,867 (1997) are useful for the treatment of anxiety.

The carbostyril derivatives disclosed in European Patent No. 226,441 have the genus of the carbostyril derivatives in the present invention, and they are useful for the treatment of hypoxia.

In addition to the above, the carbostyril derivatives disclosed in U.S. Pat. No. 4,734,416; Canadian Patent No. 1,117, 110; British Patent No. 2,017,701; German Patent Nos. 2,912, 105 and 2,953,723; Japanese Patent Kokai (Laid-open) Nos. 54-130,587 (1979), 55-127,371 (1980) and 62-149,664 (1987) have the genus of the carbosyril derivatives in the present invention, and they have antihistaminic activities and central nervous controlling activities.

It is reported that aripiprazole (7-{4-[4-(2,3-dichlorophenyl)-1-piperazinyl]butoxy}-3,4-dihydrocarbostyril, also known as, OPC-14597, BMS-337,039 and OPS-31) binds with high affinity to dopamine $D_2$ receptors and with moderate affinity to dopamine $D_3$ and 5-$HT_7$ receptors (Masashi Sasa et al., CNS Drug Reviews, Vol. 3, No. 1, pp. 24-33).

Further, it is reported that aripiprazole possesses presynaptic dopaminergic autoreceptor agonistic activity, postsynaptic $D_2$ receptor antagonistic activity, and $D_2$ receptor partial agonistic activity (T. Kikuchi, K. Tottori, Y. Uwahodo, T. Hirose, T. Miwa, Y. Oshiro and S. Morita: J. Pharmacol. Exp. Ther., Vol. 274, pp. 329, (1995); T. Inoue, M. Domae, K. Yamada and T. Furukawa: J. Pharmacol. Exp. Ther., Vol. 277, pp. 137, (1996)).

However, it has not been reported that compounds in the present invention have agonistic activity at 5-$HT_{1A}$ receptor subtype.

It has been reported that therapeutic interventions using 5-$HT_{1A}$ receptor ligands may be useful drug treatments for alcohol abuse (Mark Kleven et al., European Journal of Pharmacology, Vol. 281, (1995) pp. 219-228).

It is also reported that 5-$HT_{1A}$ agonist drugs may be useful for the treatment and/or prophylaxis of disorders associated with neuronal degeneration resulting from ischemic events in mammals (U.S. Pat. No. 5,162,375).

It is also reported that 5-$HT_{1A}$ receptor hypersensitivity could be the biological basis for the increased frequency of migraine attack in stressful and anxious conditions (Massimo Leone et al., Neuro Report, Vol. 9, pp. 2605-2608 (1998)).

It has recently been reported that (−)-(R)-2-[4-[[(3,4-dihydro-2H-1-benzopyran-2-yl)methyl]amino]-butyl]-1,2-benzisothiazol-3(2H)-one 1,1-dioxide monohydrochrolide (BAY-3702), a 5-$HT_{1A}$ receptor agonist, has neuroprotective, anxiolytic- and antidepressant-like effects in animal models (Jean De Vry et al., European Journal of Pharmacology, Vol. 357, (1998), pp. 1-8).

It is also reported that 5-$HT_{1A}$ receptor agonists appear to be broad spectrum antiemetic agents (Mary C. Wolff et al., European Journal of Pharmacology, Vol. 340, (1997), pp. 217-220; AB Alfieri et al., British Journal of Cancer, (1995), Vol. 72, pp. 1013-1015; Mary C. Wolff et al., Pharmacology Biochemistry and Behavior, 1995, Vol. 52, No. 3, pp. 571-575; James B. Lucot, European Journal of Pharmacology, 1997, Vol. 253, pp. 53-60).

Serotonin plays a role in several neuro-logical and psychiatric disorders, including Alzheimer's disease, depression, nausea and vomiting, eating disorders, and migraine. (See Rasmussen et al., "Chapter 1. Recent Progress in Serotonin 5$HT_{1A}$ Receptor Modulators", in Annual Reports in Medicinal Chemistry, Vol. 30, Section I, pp. 1-9, 1995, Academic Press, Inc.). WO 00/16777 discloses that a 5$HT_{1A}$ receptor agonist, buspirone is efficacious in treating a variety of symptoms associated with ADHD, and that combined use of a D2 receptor agonist and 5-$HT_{1A}$ agonist provides effective treatments for ADHD and Parkinson's disease.

5$HT_{1A}$ agonists are effective in the treatment of cognitive impairment in Alzheimer's disease, Parkinson's disease or senile dementia. U.S. Pat. No. 5,824,680 discloses that a 5-$HT_{1A}$ agonist, ipsapirone, is effective in treating Alzheimer's disease by improving memory. U.S. Pat. No. 4,687,772 describes that a 5-$HT_{1A}$ partial agonist, buspirone, is useful for improving short term memory in patients in need of treatment. WO 93/04681 discloses that use of 5-$HT_{1A}$ partial agonists have been used for the treatment or prevention of cognitive disorders associated with Alzheimer's disease, Parkinson's disease or senile dementia.

5$HT_{1A}$ agonists are also effective in the treatment of depression. U.S. Pat. No. 4,771,053 describes that a 5-$HT_{1A}$ receptor partial agonist, gepirone, is useful in alleviation of certain primary depressive disorders, such as severe depression, endogenous depression, major depression with melancholia, and atypical depression. WO 01/52855 discloses that the combined use of the 5-$HT_{1A}$ receptor partial agonist gepirone with an antidepressant can effectively treat depression.

The 5-$HT_{1A}$ receptor partial agonist buspirone alleviates motor disorders such as neuroleptic induced parkinsonism and extrapyramidal symptoms. These observations are disclosed in U.S. Pat. No. 4,438,119. Furthermore 5-$HT_{1A}$ agonists reverse neuroleptic-induced catalepsy in rodents, which mimic movement impairments observed in Parkinson's disease (Mark J. Millan, Journal of Pharmacology and Experimental Therapeutics, 2000, Vol. 295, p 853-861). Thus, aripiprazole can be used to manage psychosis in geriatric patients, Alzheimer's disease, Parkinson's disease or senile dementia, since it possesses potent, partial agonistic activities at $D_2$ and 5-$HT_{1A}$ receptors. In addition, these patients might not experience extrapyramidal symptoms due to this property of aripiprazole.

Heretofore, schizophrenia is understood to be caused by hyperactivity in the brain dopaminergic system. For this reason, some drugs were developed with strong dopaminergic receptor blocking activity. These typical antipsychotic drugs are effective in the treatments for the positive symptoms of schizophrenia, which include hallucinations, delusions and the like. During the last decade, a variety of atypical antipsychotic drugs have been developed, which include clozapine, risperidone, olanzapine, quetiapine. These drugs have less extrapyramidal side effects, and have other activities in addition to their DA-receptor blocking activities. In contrast to typical anti-psychotic drugs, such as chlorpromazine, haloperidol, etc., it is reported that atypical antipsychotic drugs are more effective against the negative symptoms and cognitive impairments associated with schizophrenia than typical antipsychotic drugs, and atypical antipsychotic drugs also have less extrapyramidal side effects (S. Miyamoto, G. E. Duncan, R. B. Mailman and J. A. Lieberman: Current Opinion in CPNS Investigational Drugs, Vol. 2, pp. 25, (2000)). However, even though atypical antipsychotic drugs provide a suitable pharmacotherapy for schizophrenia, certain patients are resistant to the antipsychotic therapies of these drugs. These patients may either not respond or may become refractory (i.e. may feel more anxious, depressed or cognitive dysfunction) in response to antipsychotic therapy. These treatment-resistant patients pose a problem for how a physician may provide an appropriate therapy.

At present, a number of treatment-resistant and treatment-refractory schizophrenic patients display symptoms that do not respond adequately to a variety of known effective classes and doses of typical or atypical antipsychotic drugs. Furthermore, these patients may also be inveterate schizophrenia or chronic schizophrenics who are often repeatedly admitted to and discharged from hospitals (R. R. Conely and R. W. Buchanan: Schizophr. Bull., Vol. 23, pp. 663, (1997)).

Symptoms of patients corresponding to treatment-resistant and treatment-refractory schizophrenics involve not only the positive symptoms, but also the negative symptoms and emotional disorders, as well as cognitive impairments (i.e., cognitive dysfunction or cognitive disturbances) (K. Akiyama and S. Watanabe: Jpn. J. Clin. Psychopharmacol., Vol. 3, pp. 423, (2000)).

Cognitive impairment exists separately from the psychic symptoms in a schizophrenic individual. Thus, medical treatment is therefore quite important, because the cognitive impairment may disturb the socially adaptable behavior of these individuals (C. Hagger, P. Buckley, J. T. Kenny, L. Friedman, D. Ubogy and H. Y. Meltzer: Biol. Psychiatry, Vol. 34, pp. 702, (1993); T. Sharma and D. Mockler: J. Clin. Psychopharmacol., Vol. 18, (Suppl. 1), pp. 128, (1998)).

At present, clozapine is an antipsychotic drug that is effective against treatment-resistant schizophrenia. Clozapine (marketed under the name of Clozaril) was approved in 1990 by FDA for the treatment and management of severely ill schizophrenics who failed to respond adequately to standard antipsychotic therapy (M. W. Jann: Pharmacotherapy, Vol. 11, pp. 179, (1991)). Clozapine has been reported to be effective against cognitive impairments in treatment-resistant schizophrenics (C. Hagger, P. Buckley, J. T. Kenny, L. Friedman, D. Ubogy and H. Y. Meltzer: Biol. Psychiatry, Vol. 34, pp. 702, (1993); M. A. Lee, P. A. Thompson and H. Y. Meltzer: J. Clin. Psychiatry, Vol. 55 (Suppl. B), pp. 82, (1994); D. E. M. Fujii, I. Ahmed, M. Jokumsen and J. M. Compton: J. Neuropsychiatry Clin. Neurosci., Vol. 9, pp. 240, (1997)). For example, it is reported that clozapine improves cognitive impairments in attention, response time, fluent-speech, etc. in treatment-resistant schizophrenics (M. A. Lee, P. A. Thompson and H. Y. Meltzer: J. Clin. Psychiatry, Vol. 55 (Suppl. B), pp. 82, (1994)). It has been also reported that clozapine provides effective improvements in cognitive impairments in an objective evaluation scale of the Wechsler Adult Intelligence Scale-Revised Full Scale (D. E. M. Fujii, I. Ahmed, M. Jokumsen and J. M. Compton: J. Neuropsychiatry Clin. Neurosci., Vol. 9, pp. 240, (1997)).

The $5\text{-HT}_{1A}$ receptor has been demonstrated to play a role in the therapeutic efficacy of clozapine against treatment-resistant schizophrenia and cognitive impairments. This relation ship was revealed by a binding experiment using human the $5\text{-HT}_{1A}$ receptors (S. L. Mason and G. P. Reynolds: Eur. J. Pharmacol., Vol. 221, pp. 397, (1992)). Further, in accordance with progress in molecular pharmacology, it is clearly understood that $5\text{-HT}_{1A}$ receptor agonistic activity or $5\text{-HT}_{1A}$ receptor partial agonistic activity plays an important role in treatment-resistant schizophrenia and cognitive impairments (A. Newman-Tancredi, C. Chaput, L. Verriele and M. J. Millan: Neuropharmacology, Vol. 35, pp. 119, (1996)). Additionally, it was reported that the number of $5\text{-HT}_{1A}$ receptor is increased in the prefrontal cortex of chronic schizophrenics who were classified treatment-resistant. This observation was explained by a compensatory process where by the manifestation of severe symptoms of chronic schizophrenia are a result of impaired neuronal function mediated by hypofunctional $5\text{-HT}_{1A}$ receptors (T. Hashimoto, N. Kitamura, Y. Kajimoto, Y. Shirai, O. Shirakawa, T. Mita, N. Nishino and C. Tanaka: Psychopharmacology, Vol. 112, pp. S35, (1993)). Therefore, a lowering in neuronal transmission mediated through $5\text{-HT}_{1A}$ receptors is expected in treatment-resistant schizophrenics. Thus the clinical efficacy of clozapine may be related to its partial agonist efficacy at the $5\text{-HT}_{1A}$ receptors (A. Newman-Tancredi, C. Chaput, L. Verriele and M. J. Millan: Neuropharmacology, Vol. 35, pp. 119, (1996)). $5\text{-HT}_{1A}$ receptor agonistic activity may be related to the clinical effects of clozapine, and this hypothesis is supported by a positron emission tomography study in primates which showed that clozapine interacts with brain $5\text{-HT}_{1A}$ receptors at a therapeutically effective dose (Y. H. Chou, C. Halldin and L. Farde: Int. J. Neuropsycho-pharmacol., Vol. 4 (Suppl. 3), pp. 5130, (2000)). Furthermore tandospirone, which is known as a selective $5\text{-HT}_{1A}$ receptor agonist, improved cognitive impairments in chronic schizophrenic patients (T. Sumiyoshi, M. Matsui, I. Yamashita, S, Nohara, T. Uehara, M. Kurachi and H. Y. Meltzer: J. Clin. Pharmacol., Vol. 20, pp. 386, (2000)). While, in animal tests, all reports do not always suggest that $5\text{-HT}_{1A}$ receptor agonist activity may be related to cognitive impairment, however, 8-OH-DPAT (8-hydroxy-2-(di-n-propylamino)tetralin), which is known as a selective $5\text{-HT}_{1A}$ receptor agonist, improves learning and memory impairments induced by scopolamine known as a muscarinic receptor antagonist, suggesting a relationship between $5\text{-HT}_{1A}$ receptor agonistic activity and improvements in cognitive impairments (M. Carli, P. Bonalumi, R. Samanin: Eur. J. Neurosci., Vol. 10, pp. 221, (1998); A. Meneses and E. Hong: Neurobiol. Learn. Mem., Vol. 71, pp. 207, (1999)).

Atypical antipsychotic drugs, such as risperidone and olanzapine, were marketed after clozapine, and it is reported that these drugs improve treatment-resistant schizophrenia or cognitive impairments in treatment-resistant schizophrenics (M. F. Green, B. D. Marshall, Jr., W. C. Wirshing, D. Ames, S. R. Marder, S. McGurck, R. S. Kern and J. Mintz: Am. J. Psychiatry, Vol. 154, pp. 799, (1997); G. Bondolifi, H. Dufour, M. Patris, J. P. May, U. Billeter, C. B. Eap and P. Baumann, on behalf of the risperidone Study Group: Am. J. Psychiatry, Vol. 155, pp. 499, (1998); A. Breier, S. H. Hamilton: Biol. Psychiatry, Vol. 45, pp. 403, (1999)).

In contrast to reports that clozapine was moderately effective against treatment-resistant schizophrenia, risperidone and olanzapine were not consistently superior to typical antipsychotic drugs in their effectiveness against treatment-resistant schizophrenia. Thus, risperidone and olanzapine bind with lower affinity to human 5-$HT_{1A}$ receptors (S. Miyamoto, G. E. Duncan, R. B. Mailman and J. A. Lieberman: Current Opinion in CPNS Investigational Drugs, Vol. 2, pp. 25, (2000)), and as such these drugs can not clearly perform activities through human 5-$HT_{1A}$ receptors at clinical effective doses.

Therefore, at present, it is understood that clozapine is effective against treatment-resistant schizophrenia (D. W. Bradford, M. H. Chakos, B. B. Sheitman, J. A. Lieberman: Psychiatry Annals, Vol. 28, PP-618, (1998); A. Inagaki: Jpn. J. Clin. Psychopharmacol., Vol. 3, pp. 787, (2000)).

As explained above, 5-$HT_{1A}$ receptor agonistic activity is important for improving treatment-resistant schizophrenia or cognitive impairment caused by treatment-resistant schizophrenia. Clozapine is effective against treatment-resistant schizophrenia, however, its use is limited due to its severe side-effect of producing agranulocytosis which requires patients to undergo periodical blood tests. Under these circumstances, the development of a safe anti-psychotic drug with potent, full or partial agonist activity at 5-$HT_{1A}$ receptors is earnestly desired.

The carbostyril compound in the present invention binds with high affinity and displays a potent, partial agonist activity at the 5-$HT_{1A}$ receptors and it has higher intrinsic activity (about 68%) as compared with that of clozapine. Therefore, the compound in the present invention has a 5-$HT_{1A}$ receptor agonistic activity that is more potent than the agonistic activity of clozapine. Thus, the present carbostyril compound may represent a more potent and highly safe drug for curing treatment-resistant schizophrenia, cognitive impairments caused by treatment-resistant schizophrenia, inveterate schizophrenia, cognitive impairments caused by inveterate schizophrenia, chronic schizophrenia, cognitive impairments caused by chronic schizophrenia and the like, as compared with other currently available pharmacotherapeutic treatments. That is, the compound in the present invention may prove to be a potent and safer drug therapy for treatment-resistant schizophrenia, cognitive impairments caused by treatment-resistant schizophrenia, inveterate schizophrenia, cognitive impairments caused by inveterate schizophrenia, chronic schizophrenia, or cognitive impairments caused by chronic schizophrenia, etc., which fail to respond adequately to currently available antipsychotic drugs such as chlorpromazine, haloperidol, sulpiride, fluphenazine, perphenazine, thioridazine, pimozide, zotepine, risperidone, olanzapine, quetiapine, amisulpride, etc.

In particular, the carbostyril compound in the present invention may be a potent and highly safe drug therapy against treatment-resistant schizophrenia, cognitive impairments caused by treatment-resistant schizophrenia, inveterate schizophrenia, cognitive impairments caused by inveterate schizophrenia, chronic schizophrenia or cognitive impairments caused by chronic schizophrenia, etc. which fail to respond adequately to both of 1 to 3 typical antipsychotic drugs selected from the group consisting of chlorpromazine, haloperidol and perphenazine, and one atypical antipsychotic drug selected from the group consisting of risperidone, olanzapine, quetiapine and amisulpride.

Moreover, the compound in the present invention may be a potent and highly safe drug therapy against treatment-resistant schizophrenia, cognitive impairments caused by treatment-resistant schizophrenia, inveterate schizophrenia, cognitive impairment caused by inveterate schizophrenia, chronic schizophrenia or cognitive impairment caused by chronic schizophrenia, etc. which fail to respond adequately to both of 2 typical antipsychotic drugs selected from the group consisting of chlorpromazine, haloperidol and perphenazine, and one atypical antipsychotic drug selected from the group consisting of risperidone, olanzapine, quetiapine and amisulpride.

Moreover, the compound in the present invention may be a potent and highly safe drug therapy against treatment-resistant schizophrenia, cognitive impairments caused by treatment-resistant schizophrenia, inveterate schizophrenia, cognitive impairments caused by inveterate schizophrenia, chronic schizophrenia, cognitive impairments caused by chronic schizophrenia, etc. which fail to respond adequately to both of 1 to 2 typical antipsychotic drugs selected from the group consisting of chlorpromazine and haloperidol, and one atypical antipsychotic drug selected from the group consisting of risperidone, olanzapine, quetiapine and amisulpride.

Moreover, the compound in the present invention may be a potent and highly safe drug therapy against treatment-resistant schizophrenia, cognitive impairments caused by treatment-resistant schizophrenia, inveterate schizophrenia, cognitive impairment caused by inveterate schizophrenia, chronic schizophrenia or cognitive impairment caused by chronic schizophrenia, etc. which fail to respond adequately to both of 2 typical antipsychotic drugs selected from the group consisting of chlorpromazine and haloperidol, and one atypical antipsychotic drug selected from the group consisting of risperidone, olanzapine, quetiapine and amisulpride.

SUMMARY OF THE INVENTION

It is an object of the present invention to provide a method of treating a patient suffering from a disorder of the central nervous system associated with the 5-$HT_{1A}$-receptor subtype.

DETAILED DESCRIPTION OF THE INVENTION

As the 5-$HT_{1A}$ receptor subtype agonist compound for use in accordance with the present invention, carbostyril derivatives represented by the following formula (1) are used:

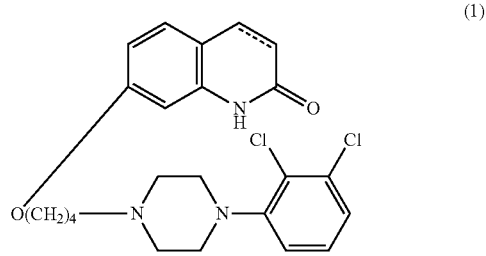

wherein the carbon-carbon bond between 3- and 4-positions in the carbostyril skeleton is a single or a double bond.

The compounds of the forgoing general formula (1) are known compounds, which are disclosed in publication such as U.S. Pat. No. 5,006,528 or which can be readily prepared by the processes described in the above publication.

The carbostyril derivative represented by the formula (1) in the present invention can easily be converted into its acid-addition salt by reacting it with a pharmaceutically acceptable acid. Examples of such acid include inorganic acids, such as hydrochloric acid, sulfuric acid, phosphoric acid, hydrobromic acid and the like; organic acids, such as oxalic acid, maleic acid, fumaric acid, malic acid, tartaric acid, citric acid, benzoic acid and the like.

The solvent of solvates is a solvent conventionally used in recrystallization. Examples of solvates include hemihydrates, hydrates, and alcoholates, such as ethanolates, methanolates, isopropanolates and the like.

The desired compounds, prepared by the reactions mentioned above, can easily be isolated and purified by usual separation procedures such as solvent extraction, dilution, recrystallization, column chromatography, preparative thin layer chromatography and the like.

The potent, partial 5-$HT_{1A}$ receptor agonist in the present invention is useful for various disorders of the central nervous system associated with the 5-$HT_{1A}$ receptor subtype that induces bipolar disorders, such as bipolar I disorder with most recent hypomanic, manic, mixed, depressed or unspecified episode; bipolar II disorder with recurrent major depressive episodes with hypomanic episodes, and cyclothymic disorder; depression, such as endogenous depression, major depression, melancholia, and treatment-resistant depression; panic disorder; obsessive compulsive disorder (OCD); sleep disorders; sexual dysfunction; alcohol abuse and drug addiction; cognitive impairment; neurodegenerative diseases, such as Alzheimer's disease, Parkinson's disease and the like, cognitive impairments caused by neurodegenerative diseases such as Alzheimer's disease, Parkinson's disease and related disorders; emesis; motion sickness; obesity; migraine; autism; Down's syndrome; attention-deficit hyper-activity disorder (ADHD); treatment-resistant, inveterate or chronic schizophrenia, (which fail to respond adequately to currently available antipsychotic drugs); cognitive impairments caused by treatment-resistant schizophrenia, inveterate schizophrenia or chronic schizophrenia and the like.

Compounds of the present invention may be suitably prepared into pharmaceutically acceptable formulations (see U.S. Pat. No. 5,006,528, European Patent No. 367,141 and Japanese Kokai (Laid-open) 7-304,740 (1995), and Japanese Patent Application No. 2000-194976 incorporated by reference herein).

The dosage of these pharmaceutical preparations of the invention may be selected appropriately depending on the method of administration, the patient's age, sex and other factors, severity of the disease and other factors. Generally, however, the daily dose of the active ingredient compound is preferably within the range of about 0.0001 to about 50 mg per kilogram of body weight. It is desirable that the active ingredient compound be contained in each unit dosage form in an amount of about 0.001 to about 1,000 mg, particularly 0.01 to 100 mg, more particularly 0.1 to 50 mg, yet more particularly 1 mg to 20 mg.

Pharmacological Tests
1. Materials and Methods
  1.1 Test Compound
  7-{4-[4-(2,3-Dichlorophenyl)-1-piperazinyl]-butoxy}-3,4-dihydrocarbostyril (aripiprazole) was used as test compound.
  1.2 Reference Compounds
  Serotonin (5-HT) and WAY-100635 (N-[2-[4-(2-methoxyphenyl)-1-piperazinyl]ethyl]-N-(2-pyridimyl)-cyclohexanecarboxamide, a 5-$HT_{1A}$ receptor antagonist, manufactured by RBI (Natick, Mass.) were used as reference compounds.
  1.3 Vehicle
  Dimethyl sulfoxide (DMSO) manufactured by Sigma Chemical Co. (St. Louis, Mo.) was used as vehicle.
  1.4 Preparation of Test and Reference Compounds
  Test compound was dissolved in 100% dimethyl sulfoxide (DMSO) to yield 100 μM stock solutions (final concentration of DMSO in all tubes containing test compound was 1%, v/v).

All other reference compounds were prepared by the same method using double-distilled water rather than DMSO.
  1.5 Experimental Procedure for the [$^{35}$S]GTPγS Binding Assay
  Test and reference compounds were studied in triplicate at 10 different concentrations (0.01, 0.1, 1, 5, 10, 50, 100, 1000, 10000 and 50000 nM) for their effects upon basal [$^{35}$S]GTPγS binding to h5-$HT_{1A}$ CHO cell membranes. Reactions were performed in 5 ml glass test tubes containing 8 μl of test/reference drug mixed with 792 μl of buffer (25 mM Tris HCl, 50 mM NaCl, 5 mM $MgCl_2$, 0.1 mM EGTA, pH=7.4) containing GDP (1 μM), [$^{35}$S]GTPγS (0.1 nM) and h5-$HT_{1A}$ CHO cell membranes (10 μg protein/reaction; NEN Life Science Products, Boston, Mass.; catalog #CRM035, lot # 501-60024, GenBank # X13556). Reactions proceeded for 60 min at room temperature and were terminated by rapid filtration through Whatman GF/B filter paper, using a Brandel harvester and 4×3 ml ice-cold buffer washes. $^{35}$S radio-activity bound to the filter paper was measured using liquid scintillation counting (1272 Clinigamma, LKB/Wallach).
  1.6 Experimental Procedure to Determine the Binding Affinity of Test compound (aripiprazole) at the h5-$HT_{1A}$ Receptor
  Test compound was studied in triplicate at 10 different concentrations (0.01, 0.1, 1, 10, 50, 100, 500, 1000, 5000 and 10000 nM) to determine its displacement of [$^3$H]8-OH-DPAT (1 nM; NEN Life Sciences; catalog #NET 929, lot # 3406035, Specific Activity=124.9 Ci/mmol) binding to h5-$HT_{1A}$ receptors in CHO cell membranes (15-20 μg protein; NEN Life Science Products, catalog # CRM035, lot # 501-60024). Membranes (396 μl) were incubated in 5 ml glass tubes containing [$^3$H]8-OH-DPAT (396 μl), test compound or vehicle (8 μl) and buffer A (50 mM Tris.HCl, 10 mM $MgSO_4$, 0.5 mM EDTA, 0.1% (w/v) ascorbic acid, pH=7.4). All assays proceeded for 60 min at room temperature and were terminated by rapid filtration through Whatman GF/B filter paper (pre-soaked in buffer B; 50 mM'Tris.HCl, pH=7.4), using a Brandel harvester and 4×1 ml ice-cold washes with buffer B. Non-specific binding was determined in the presence of 10 μM (+)8-OH-DPAT.
  1.7 Parameters Determined
  Serotonin (5-HT) is a full 5-$HT_{1A}$ receptor agonist which stimulates increases in basal [$^{35}$S]GTPγS binding to h5-$HT_{1A}$ receptors in recombinant CHO cell membranes. Test compound was studied at 10 concentrations to determine their effects upon basal [$^{35}$S]GTPγS binding relative to that produced by 10 μM 5-HT. The relative potency ($EC_{50}$, 95% confidence interval) and intrinsic agonist activity (% of $E_{max}$ for 10 μM 5-HT) was calculated for each compound by computerized non-linear regression analysis of complete concentration-effect data. The binding affinity of test compound at the h5-$HT_{1A}$ receptor was determined by its ability to prevent [$^3$]8-OH-DPAT binding to CHO cell membranes that express this receptor. Non-linear regression analysis of the competition binding data was used to calculate an inhibition constant ($IC_{50}$, 95% confidence interval), which is the concentration of test compound that occupies half of the h5-$HT_{1A}$ sites specifically bound by [$^3$H]8-OH-DPAT. The affinity of h5-$HT_{1A}$ receptors for test compound (Ki, 95% confidence interval) was calculated by the equation, $Ki=(IC_{50})/(1+([[^3H]8\text{-}OH\text{-}DPAT]/Kd))$, where the Kd for [$^3$H]8-OH-DPAT at h5-$HT_{1A}$=0.69 nM (NEN Life Sciences). All estimates of drug binding affinity, potency and intrinsic efficacy at the h5-$HT_{1A}$ receptor were calculated using GraphPad Prism version 3.00 for Windows (GraphPad Software, San Diego, Calif.).

2. Results

Test compound and 5-HT produced concentration-dependent increases above basal [$^{35}$S]GTPγS binding. 1% DMSO tested alone had no effect upon basal or drug-induced [$^{35}$S] GTRγS binding.

Test compound (EC$_{50}$=2.12 nM), 5-HT (EC$_{50}$=3.67 nM), potently stimulated basal [$^{35}$S]GTPγS binding. Potency and intrinsic agonist efficacy estimates were derived by non-linear regression analysis with correlation coefficients (r$^2$)>0.98 in each case (Table 1). Test compound exerted partial agonist efficacies in the 65-70% range. WAY-100635 produced no significant change (unpaired Student's t-test) in basal [$^{35}$S] GTPγS binding at all concentrations tested (Table 1). WAY-100635 did, however, completely inhibit the effects of 5-HT and test compound upon [$^{35}$S]GTPγS binding to h5-HT$_{1A}$ receptors in CHO cell membranes (Table 2). Tables 1 and 2 are shown below.

Test compound demonstrated high affinity binding to h5-HT$_{1A}$ receptors in CHO cell membranes (IC$_{50}$=4.03 nM, 95% confidence interval=2.67 to 6.08 nM; Ki=1.65 nM, 95% confidence interval=1.09 to 2.48 nM).

TABLE 1

Potency (EC$_{50}$) and Intrinsic Agonist Efficacy (E$_{max}$) of Test compound and Reference Drugs in a h5-HT$_{1A}$ [$^{35}$S] GTPγS CHO-cell Membrane Binding Assay.

| Drug | EC$_{50}$, nM (95% Confidence Interval) | E$_{max}$ (% ± SEM) | Goodness of Fit (r$^2$) |
|---|---|---|---|
| Test Compound | 2.12 (0.87 to 5.16) | 68.13 ± 3.16 | 0.986 |
| 5-HT | 3.67 (1.56 to 8.63) | 98.35 ± 4.47 | 0.986 |
| WAY-100635 | — | — | — |

TABLE 2

Inhibitory Potency (IC$_{50}$) of WAY-100635 versus 1 µM Concentration of 5-HT and Test compound in a h5-HT$_{1A}$ [$^{35}$S] GTPγS CHO-cell Membrane Binding Assay.

| Drug Combination | WAY-100635 Inhibition Potency, IC$_{50}$, nM (95% Confidence Interval) | Goodness of Fit (r$^2$) |
|---|---|---|
| 5-HT + WAY-100635 | 217.1 (127.4 to 369.7) | 0.988 |
| Test compound + WAY-100635 | 392.2 (224.1 to 686.2) | 0.989 |

What is claimed is:

1. A method of treating a patient suffering from, obsessive compulsive disorder (OCD), which comprises administering to said patient a therapeutically effective amount of a carbostyril compound of formula (1), or a pharmaceutically acceptable salt, or a solvate thereof selected from hemihydrates, hydrates, and alcoholates, wherein said patient is a mammal:

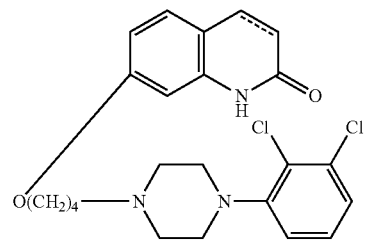

(1)

wherein the carbon-carbon bond between 3- and 4-positions in the carbostyril skeleton is a single or a double bond.

2. The method according to claim 1, wherein the carbostyril compound is 7-{4-[4-(2,3-dichlorophenyl)-1-piperazinyl]butoxyl}-3,4-dihydrocarbostyril.

3. A method of treating a patient suffering from alcohol addiction, which comprises administering to said patient a therapeutically effective amount of a carbostyril compound of formula (1), or a pharmaceutically acceptable salt, or a solvate thereof selected from hemihyd rates, hydrates, and alcoholates, wherein said patient is a mammal:

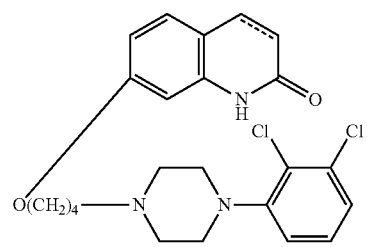

(1)

wherein the carbon-carbon bond between 3- and 4- positions in the carbostyril skeleton is a single or a double bond.

4. The method according to claim 3, wherein the carbostyril compound is 7-{4-[4-(2,3-diichlorophenyl)-1-piperazinyl]butoxy}-3,4-dihydrocarbostyril.

5. A method of treating a patient suffering from drug addiction, which comprises administering to said patient a therapeutically effective amount of a carbostyril compound of formula (1), or a pharmaceutically acceptable salt, or a solvate thereof selected from hemihyd rates, hydrates, and alcoholates, wherein said patient is a mammal:

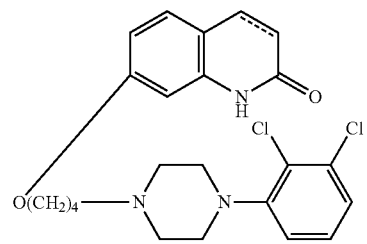

(1)

wherein the carbon-carbon bond between 3- and 4- positions in the carbostyril skeleton is a single or a double bond.

6. The method according to claim 5, wherein the carbostyril compound is 7-{4-[4-(2,3-dichlorophenyl)-1-piperazinyl]butoxyl}-3,4-dihydrocarbostyril.

* * * * *

UNITED STATES PATENT AND TRADEMARK OFFICE
CERTIFICATE OF CORRECTION

| | | |
|---|---|---|
| PATENT NO. | : 8,030,312 B2 | Page 1 of 1 |
| APPLICATION NO. | : 10/876605 | |
| DATED | : October 4, 2011 | |
| INVENTOR(S) | : Jordan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 152 days.

Signed and Sealed this
Sixth Day of March, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,030,312 B2 | Page 1 of 1 |
| APPLICATION NO. | : 10/876605 | |
| DATED | : October 4, 2011 | |
| INVENTOR(S) | : Jordan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 435 days.

Signed and Sealed this
Seventeenth Day of March, 2020

Andrei Iancu
*Director of the United States Patent and Trademark Office*